US00PP22599P2

(12) United States Plant Patent
van der Knaap

(10) Patent No.: US PP22,599 P2
(45) Date of Patent: Mar. 20, 2012

(54) *SPATHIPHYLLUM* PLANT NAMED 'SPADALU'

(50) Latin Name: *Spathiphyllum Schott*
Varietal Denomination: Spadalu

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 12/804,006

(22) Filed: Jul. 12, 2010

(51) Int. Cl.
*A01H 5/00* (2006.01)

(52) U.S. Cl. ..... Plt./364

(58) Field of Classification Search ..... Plt./364
See application file for complete search history.

(56) References Cited

OTHER PUBLICATIONS

Upov-rom Plant Variety Database 2011/01. PBR 20081386 published Aug. 15, 2008 in the European Community, one page.*

* cited by examiner

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Spathiphyllum* plant named 'Spadalu', characterized by its upright, outwardly arching and uniform plant habit; freely clumping growth habit; bushy and dense plants; glossy dark green-colored leaves; freely flowering habit; white-colored spathes that are positioned above and between the foliar plane on strong and erect scapes; and good inflorescence longevity.

2 Drawing Sheets

Botanical designation: *Spathiphyllum Schott.*
Cultivar denomination: 'SPADALU'.

BACKGROUND OF THE INVENTION

The present invention relates to a new and distinct cultivar of *Spathiphyllum* plant, botanically known as *Spathiphyllum Schott.* and hereinafter referred to by the name 'Spadalu'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in September, 2004, in Naaldwijk, The Netherlands of a proprietary selection of *Spathiphyllum Schott.* identified as code number 19961243-001, not patented, as the female, or seed, parent with a proprietary selection of *Spathiphyllum Schott.* identified as code number 20020969-001, not patented, as the male, or pollen, parent. The new *Spathiphyllum* plant was discovered and selected by the Inventor as a single flowering plant within the progeny of the stated cross-pollination in a controlled greenhouse environment in Naaldwijk, The Netherlands in March, 2006.

Asexual reproduction of the new *Spathiphyllum* plant by tissue culture in a controlled environment in Maasdijk, The Netherlands since June, 2006 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Spadalu'. These characteristics in combination distinguish 'Spadalu' as a new and distinct cultivar of *Spathiphyllum* plant:

1. Upright, outwardly arching and uniform plant habit.
2. Freely clumping growth habit; bushy and dense plants.
3. Glossy dark green-colored leaves.
4. Freely flowering habit.
5. White-colored spathes that are positioned above and between the foliar plane on strong and erect scapes.
6. Good inflorescence longevity.

Plants of the new *Spathiphyllum* differ from plants of the female parent selection in the following characteristics:

1. Plants of the new *Spathiphyllum* are more freely clumping than plants of the female parent selection.
2. Plants of the new *Spathiphyllum* have darker green-colored leaves than plants of the female parent selection.
3. Plants of the new *Spathiphyllum* have glossier leaves than plants of the female parent selection.

Plants of the new *Spathiphyllum* differ from plants of the male parent selection in the following characteristics:

1. Plants of the new *Spathiphyllum* are more freely clumping than plants of the male parent selection.
2. Plants of the new *Spathiphyllum* have lighter green-colored leaves than plants of the male parent selection.
3. Plants of the new *Spathiphyllum* have glossier leaves than plants of the male parent selection.

Plants of the new *Spathiphyllum* can also be compared to plants of *Spathiphyllum* spp. 'Sparego', disclosed in U.S. Plant Pat. No. 11,457. In side-by-side comparisons conducted in Naaldwijk, The Netherlands, plants of the new *Spathiphyllum* differed from plants of 'Sparego' in the following characteristics:

1. Plants of the new *Spathiphyllum* were more freely clumping than plants of 'Sparego'.
2. Plants of the new *Spathiphyllum* had smaller spathes than plants of 'Sparego'.
3. Spathes of plants of the new *Spathiphyllum* were whiter in color than spathes of plants of 'Sparego'.

BRIEF DESCRIPTION OF THE PHOTOGRAPHS

The accompanying photographs illustrate the overall appearance of the new *Spathiphyllum* plant. These photographs show the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet is a side perspective view of a typical plant of 'Spadalu' grown in a container.

The photograph on the second sheet is a close-up view of a typical inflorescence of 'Spadalu'.

DETAILED BOTANICAL DESCRIPTION

The aforementioned photographs and following observations and measurements describe plants grown during the spring in 17-cm containers in a glass-covered greenhouse in Naaldwijk, The Netherlands. Plants were grown under conditions and practices which approximate those generally used in commercial *Spathiphyllum* production. During the production of the plants, day temperatures ranged from about 19° C. to 24° C., night temperatures ranged from about 19° C. to 22° C. and light levels were about five kilolux. Plants were 36 weeks old when the photographs and the detailed description were taken. In the following description, color references are made to The Royal Horticultural Society Colour Chart, 2007 Edition, except where general terms of ordinary dictionary significance are used.

Botanical classification: *Spathiphyllum Schott.* 'Spadalu'.

Parentage:

*Female, or seed, parent.*—Proprietary selection of *Spathiphyllum Schott*. identified as code number 19961243-001, not patented.

*Male, or pollen, parent.*—Proprietary selection of *Spathiphyllum Schott.* identified as code number 20020969-001, not patented.

Propagation:

*Type.*—By tissue culture.

*Time to initiate roots.*—About eleven days at 23° C.

*Time to produce a rooted young plant, summer.*—About 215 days at 21° C.

*Time to produce a rooted young plant, winter.*—About 240 days at 21° C.

*Root description.*—Medium in thickness, fibrous; white, close to 155D, in color.

*Rooting habit.*—Moderately branching, moderately dense.

Plant description:

*Plant shape.*—Upright and outwardly arching plant habit, uniform inverted triangular habit.

*Growth habit.*—Freely clumping, bushy and dense growth habit; about six clumps per plant; moderately vigorous growth habit.

*Plant height, from soil level to top of leaf plane.*—About 51 cm.

*Plant height, from soil level to top of inflorescences.*—About 72.5 cm.

*Plant diameter or spread.*—About 61.7 cm.

*Foliage description.*—Arrangement: Alternate; simple. Length: About 28.3 cm. Width: About 11.9 cm. Shape: Narrowly ovate to ovate. Apex: Narrowly apiculate. Base: Attenuate. Margin: Entire; slightly undulate. Texture, upper and lower surfaces: Smooth, glabrous; slightly leathery. Luster, upper and lower surfaces: Glossy. Venation pattern: Pinnate. Color: Developing leaves, upper surface: Between 137A and 146A. Developing leaves, lower surface: Close to 147B. Fully expanded leaves, upper surface: Between N137D and 147A; venation, close to 146A. Fully expanded leaves, lower surface: Close to 147B; venation, close to 144A. Petiole: Length (excluding geniculum): About 17.8 cm. Diameter, just below geniculum: About 5 mm. Diameter, at plant base: About 1 cm. Texture: Smooth, glabrous. Luster: Slightly glossy. Color, upper and lower surfaces: Close to 137A. Geniculum length: About 2.8 cm. Geniculum diameter: About 6 mm. Geniculum texture: Smooth, glabrous. Geniculum luster: Slightly glossy. Geniculum color, upper and lower surfaces: Between 144C and 146C. Wing length: About 16.2 cm. Wing diameter: About 7 mm. Wing color: Close to N137A.

Inflorescence description:

*Inflorescence arrangement and flowering habit.*—Slightly cupped erect spathes with columnar spadices held above and between the foliar plane on strong and erect scapes; flowering structures arise from leaf axils; plants begin flowering about six months after planting; freely and continuous flowering year-round in The Netherlands; typically about six inflorescences develop per plant.

*Fragrance.*—Faint; sweet and pleasant.

*Inflorescence longevity.*—Inflorescences last about three weeks on the plant; inflorescences persistent.

*Spathe.*—Length: About 17 cm. Width: About 9.6 cm. Shape: Ovate. Apex: Apiculate; twisting. Base: Obtuse with truncate tendencies. Margin: Entire. Texture, upper and lower surfaces: Smooth, glabrous; slightly leathery. Luster, upper and lower surfaces: Glossy. Color: When developing, front surface: Close to 155A to 155B; at the apex, close to 144A to 144B. When developing, rear surface: Close to 155A to 155B; main vein and at the apex, close to 144A. Fully developed, front surface: Close to NN155A; main vein and towards the apex, close to 145B; at the apex, close to 137B; with development, color becoming closer to 144B. Fully developed, rear surface: Close to NN155A; main vein and at the apex, close to 143A to 143B.

*Spadix.*—Length: About 6.1 cm. Diameter: About 1.2 cm. Shape: Columnar, tapering towards the apex; apex, obtuse; base, obtuse; cross-section, rounded. Aspect: Mostly erect. Color: Immature: Between 150D and 157A. Mature: Close to 155A. Flowers: Quantity per spadix: Numerous, about 175. Shape: Rounded. Height: About 2.5 mm. Diameter: About 3 mm. Anther color: Close to 155A. Pollen amount: Scarce. Pollen color: Close to 155D. Stigma shape: Ovoid. Stigma color: Close to NN155A. Ovary color: Close to 155A.

*Scape.*—Length: About 52.2 cm. Diameter: About 5 mm. Strength: Strong. Texture: Smooth, glabrous.

Aspect: Erect to about 15° from vertical. Color: Between 143A and 146A; towards the base, close to 145A to 145B.

*Seed and fruit.*—Seed and fruit development has not been observed on plants of the new *Spathiphyllum.*

Disease/pest resistance: Plants of the new *Spathiphyllum* have not been observed to be resistant to pathogens or pests common to *Spathiphyllum.*

Temperature tolerance: Plants of the new *Spathiphyllum* have been observed to be tolerant to temperatures ranging from about 15° C. to about 36° C.

It is claimed:

1. A new and distinct *Spathiphyllum* plant named 'Spadalu' as illustrated and described.

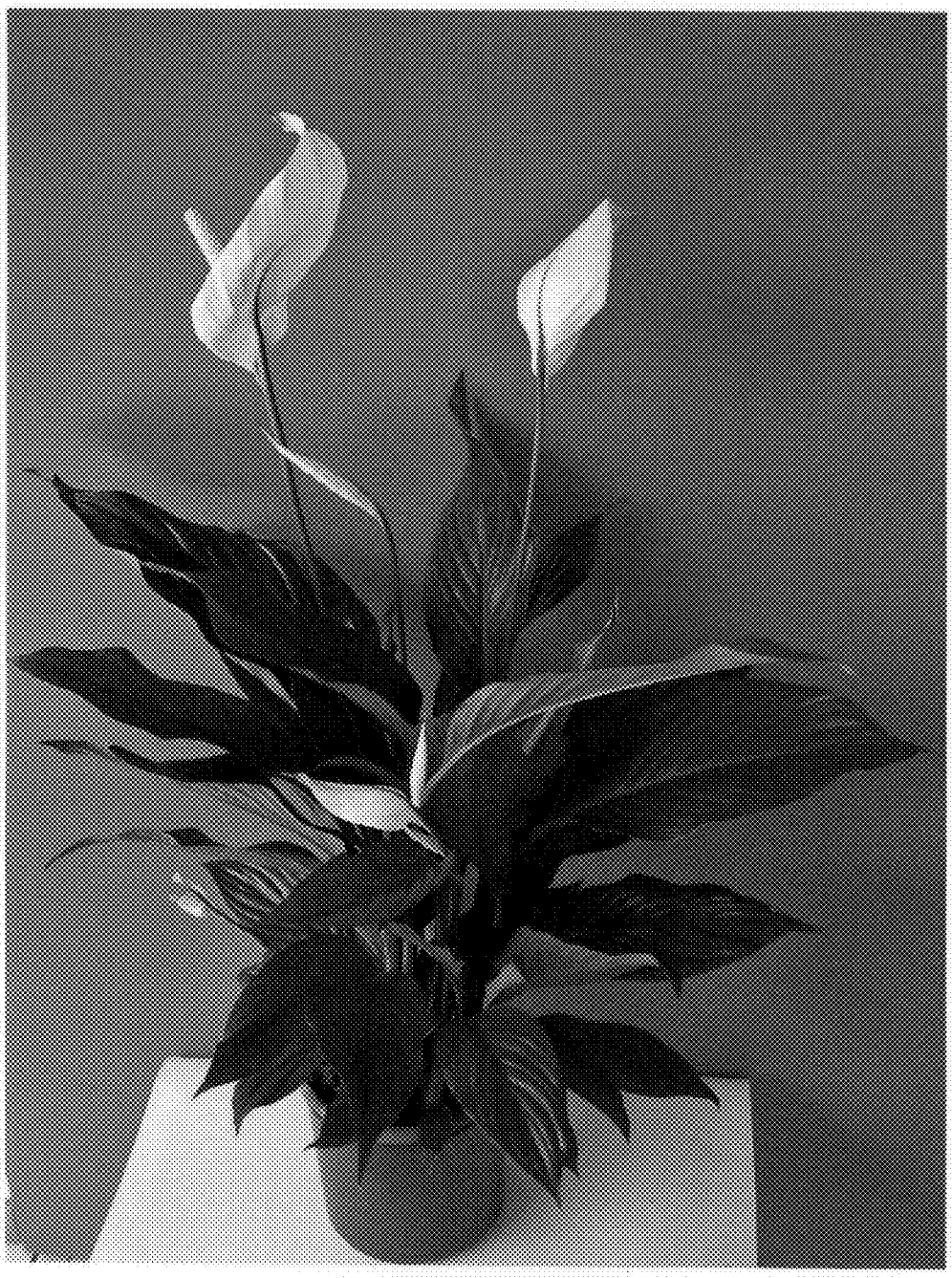

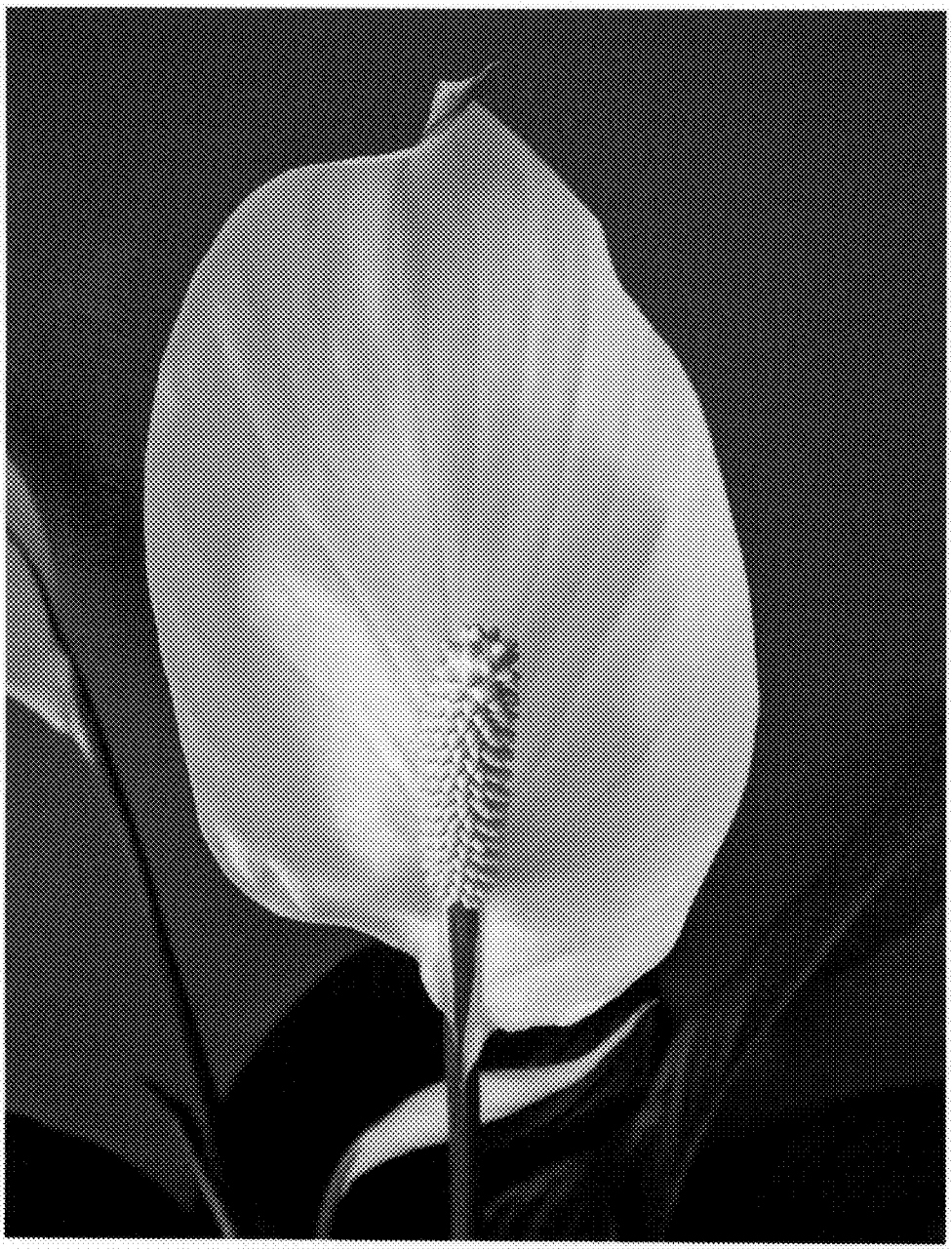

* * * * *